United States Patent
Keefer et al.

(10) Patent No.: US 9,999,428 B2
(45) Date of Patent: Jun. 19, 2018

(54) ORTHOPAEDIC SURGICAL INSTRUMENT SYSTEM AND METHOD FOR SURGICALLY PREPARING A PATIENTS BONE

(71) Applicant: DEPUY SYNTHES PRODUCTS, INC., Raynham, MA (US)

(72) Inventors: Ryan C. Keefer, Warsaw, IN (US); Lauren Flakne, Warsaw, IN (US); John Cuneo, Norton, MA (US); Michael J. Fortin, Acushnet, MA (US); Thomas J. Blumenfeld, Sacramento, CA (US); Robert T. Trousdale, Rochester, MN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 368 days.

(21) Appl. No.: 14/788,052

(22) Filed: Jun. 30, 2015

(65) Prior Publication Data
US 2017/0000503 A1    Jan. 5, 2017

(51) Int. Cl.
*A61B 17/58* (2006.01)
*A61B 17/17* (2006.01)
*A61B 17/16* (2006.01)
*A61B 17/15* (2006.01)

(52) U.S. Cl.
CPC .......... *A61B 17/17* (2013.01); *A61B 17/1615* (2013.01); *A61B 17/1675* (2013.01); *A61B 17/1764* (2013.01); *A61B 17/157* (2013.01); *A61B 2017/1602* (2013.01)

(58) Field of Classification Search
CPC .............. A61B 17/157; A61B 17/1764; A61B 17/1615; A61B 17/1675; A61B 2017/1602
See application file for complete search history.

(56) References Cited

U.S. PATENT DOCUMENTS

| 5,486,180 | A | * | 1/1996 | Dietz | A61B 17/1764 606/86 R |
| 5,908,424 | A | * | 6/1999 | Bertin | A61B 17/1764 606/88 |
| 6,554,838 | B2 | * | 4/2003 | McGovern | A61B 17/1764 606/87 |
| 6,994,730 | B2 | * | 2/2006 | Posner | A61B 17/155 623/20.32 |

(Continued)

FOREIGN PATENT DOCUMENTS

| EP | 0554959 A1 | 8/1993 |
| EP | 2181672 A1 | 5/2010 |

OTHER PUBLICATIONS

Extended European Search Report, European Application No. 16176839.5-1664 / 3146919, dated Jun. 29, 2017, 10 pages.

(Continued)

*Primary Examiner* — David H Willse
*Assistant Examiner* — Javier Blanco
(74) *Attorney, Agent, or Firm* — Barnes & Thornburg LLP

(57) ABSTRACT

An orthopedic surgical instrument system for use in preparing a patient's bone is disclosed. The surgical instrument includes a cutting guide block configured to be secured to a surgically-prepared surface of the patient's bone, and a cutting tool to be used in conjunction with the cutting guide block to resect a section of the patient's bone. A method of performing an orthopedic surgery is also disclosed.

10 Claims, 13 Drawing Sheets

(56) References Cited

U.S. PATENT DOCUMENTS

| | | | | |
|---|---|---|---|---|
| 2003/0236521 A1* | 12/2003 | Brown | ............... | A61B 17/1615 606/80 |
| 2005/0192588 A1* | 9/2005 | Garcia | ................. | A61B 17/155 606/88 |
| 2006/0089621 A1* | 4/2006 | Fard | ................... | A61B 17/1615 606/1 |
| 2006/0276796 A1* | 12/2006 | Creger | ............... | A61B 17/1767 606/79 |
| 2006/0293682 A1* | 12/2006 | Justin | ................. | A61B 17/1615 606/88 |
| 2008/0234683 A1* | 9/2008 | May | ....................... | A61B 17/17 606/87 |
| 2010/0036383 A1* | 2/2010 | Major | .................. | A61B 17/155 606/89 |
| 2012/0259335 A1* | 10/2012 | Scifert | ................. | A61B 17/155 606/80 |
| 2013/0041376 A1* | 2/2013 | Neal | .................. | A61B 17/1633 606/79 |
| 2014/0114320 A1 | 4/2014 | Kurtz | | |

OTHER PUBLICATIONS

Zimmer Trabecular Metal Tibial and Femoral Cones Surgical Techniques, 97-5450-009-00 1104-K13, 44 pages (2011).

* cited by examiner

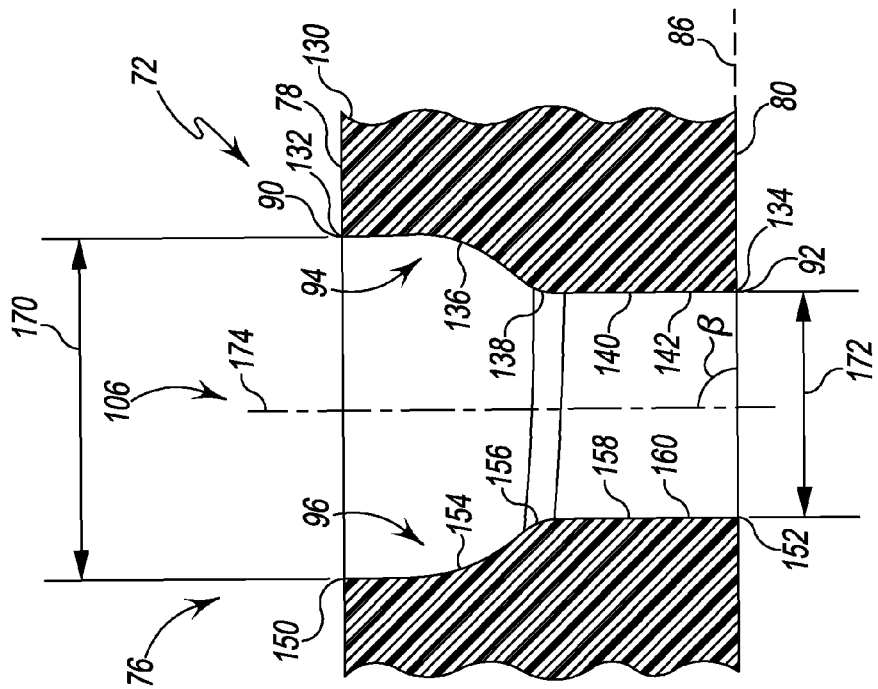
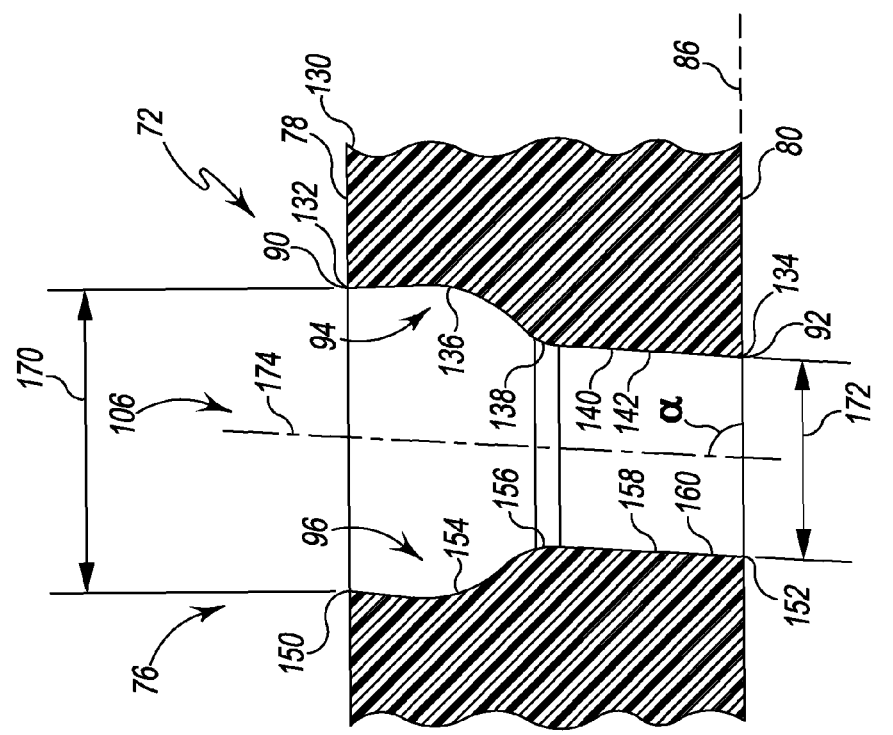

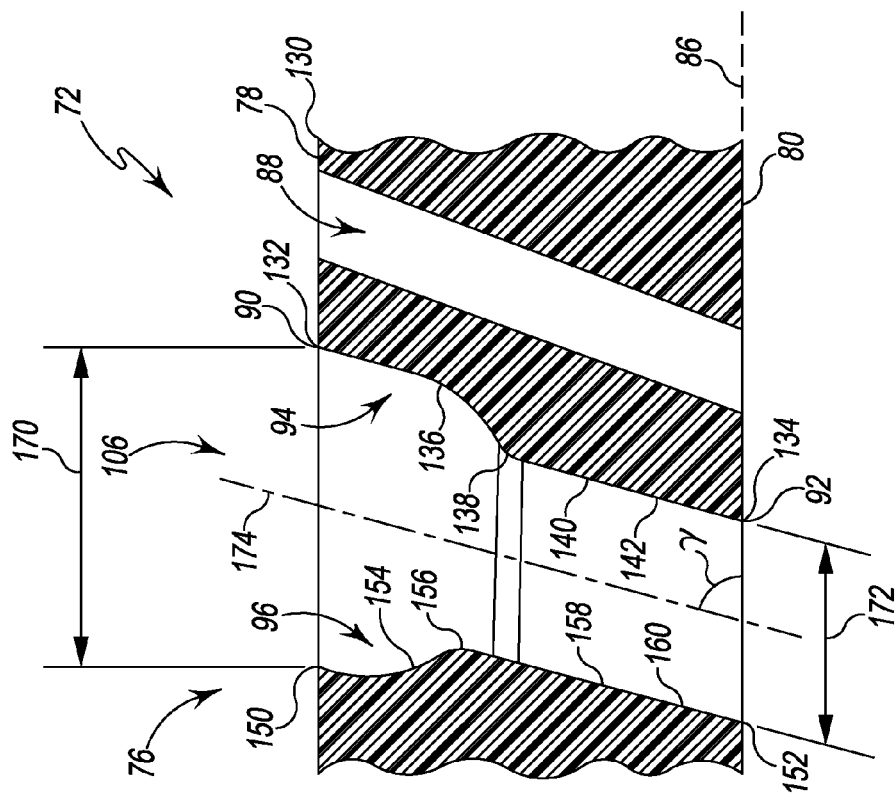
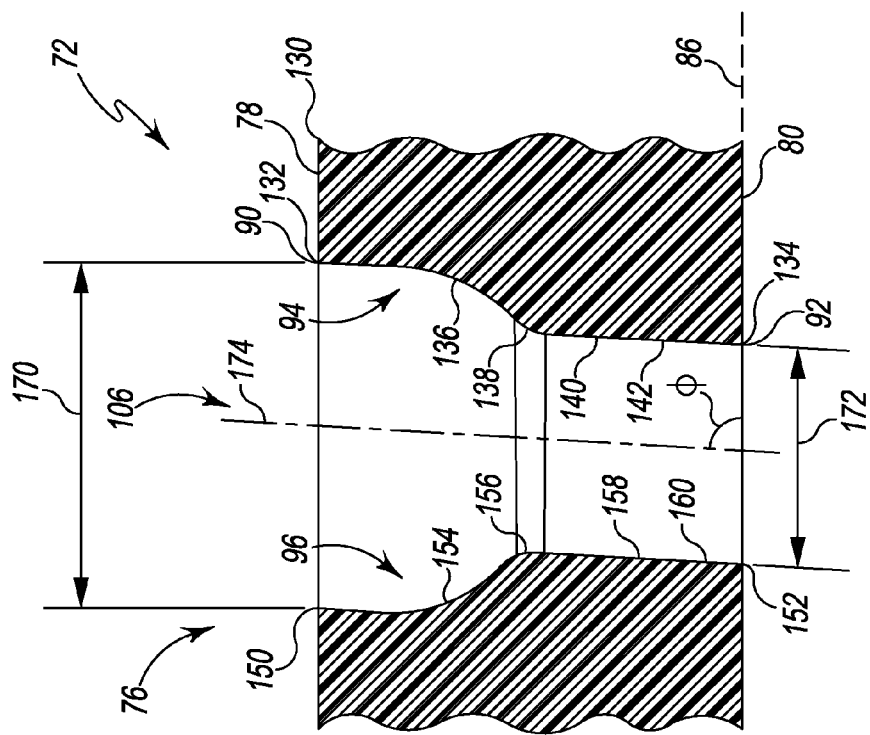

ORTHOPAEDIC SURGICAL INSTRUMENT SYSTEM AND METHOD FOR SURGICALLY PREPARING A PATIENTS BONE

TECHNICAL FIELD

The present disclosure relates generally to orthopaedic surgical instruments and, more particularly, to surgical instruments used to prepare a patient's tibia or femur to receive an orthopaedic prosthetic component.

BACKGROUND

Joint arthroplasty is a well-known surgical procedure by which a diseased or damaged natural joint is replaced by a prosthetic joint. A typical knee prosthesis includes a tibial tray, a femoral component, and a polymer insert or bearing positioned between the tibial tray and the femoral component. Over time, an implanted prosthesis can cause damage to the surrounding bone through component loosening, subsidence and osteolysis. A revision total knee arthroplasty may be used to replace the original knee prosthesis and account for bone defects now present in the patient. A primary or a revision knee prosthesis may include a cone implant, which is a modular device used to correct for bone defects and provide structural support for the other components of the prosthesis, such as, for example, a tibial tray or a femoral component.

SUMMARY

According to one aspect of the disclosure, an orthopaedic surgical instrument system is disclosed. The system comprises a cutting tool including a shank, a shaft extending distally from the shank, the shaft having a plurality of cutting flutes defined at its distal end, and an outer sleeve coupled to the shaft. The system also comprises a cutting guide block for use with the cutting tool. The cutting guide block comprises a superior surface, an inferior surface positioned opposite the superior surface that defines an imaginary plane, and a slot extending through the superior surface and the inferior surface. The slot defines a cutting guide that extends from a first end to a second end that is sized to receive the cutting tool.

When the slot is viewed in a cross-sectional plane extending perpendicular to the imaginary plane at each of a plurality of points between the first end and the second end, the slot has a central axis that extends through the superior surface and the inferior surface, and an angle is defined between the central axis and the imaginary plane. The magnitude of the angle is non-constant between the first end of the cutting guide and the second end of the cutting guide such that the pitch of the cutting tool is adjusted as the cutting tool is moved along the cutting guide.

In some embodiments, the slot may be defined between a first inner wall extending from a first opening defined in the superior surface and a second opening defined in the inferior surface, and a second inner wall extending from the first opening defined in the superior surface and the second opening defined in the inferior surface. The central axis may be positioned between, and extend parallel to, portions of the first inner wall and the second inner wall when the slot is viewed in any of the cross-sectional planes extending perpendicular to the imaginary plane.

Additionally, in some embodiments, when the slot is viewed in any of the cross-sectional planes extending perpendicular to the imaginary plane, a first width of the slot may be defined between a superior edge of the first inner wall and a superior edge of the second inner wall, and a second width of the slot may be defined between an inferior edge of the first inner wall and an inferior edge of the second inner wall. The second width of the slot may be less than the first width.

In some embodiments, when the slot is viewed in any of the cross-sectional planes extending perpendicular to the imaginary plane, the first inner wall may include a first section extending inwardly from the superior edge of the first inner wall to a transition surface and a second section extending inwardly from the inferior edge of the first inner wall to the transition surface. The first section may be curved and the second section may define a straight imaginary line.

Additionally, in some embodiments, when the slot is viewed in any of the cross-sectional planes extending perpendicular to the imaginary plane, the second inner wall may include a first section extending inwardly from the superior edge of the second inner wall to a transition surface and a second section extending inwardly from the inferior edge of the second inner wall to the transition surface. The first section of the second inner wall may be curved and the second section of the second inner wall may define a straight imaginary line extending parallel to the straight imaginary line defined by the second section of the first inner wall. In some embodiments, the transition surfaces may define a beveled groove sized to engage the outer sleeve of the cutting tool.

In some embodiments, the slot may include a first slot section extending anteriorly from the first end, a second slot section extending laterally from the second end, and a third slot section connecting the first slot section to the second slot section. Additionally, in some embodiments, the third slot section may include a first arced section connected to the first slot section, a second arced section connected to the second slot section, and a substantially straight section extending in a medial-lateral direction and connecting the first arced section and the second arced section.

In some embodiments, when the first arced section of the slot is viewed in a cross-sectional plane extending in a medial-lateral direction perpendicular to the imaginary plane, the angle defined between the central axis and the imaginary plane may have a first magnitude. When the straight section of the slot is viewed in a cross-sectional plane extending in an anterior-posterior direction perpendicular to the imaginary plane, the angle defined between the central axis and the imaginary plane may have a second magnitude that is greater than the first magnitude. In some embodiments, the second magnitude may be less than 90 degrees.

In some embodiments, when the first slot section of the slot is viewed in a cross-sectional plane extending in a medial-lateral direction perpendicular to the imaginary plane, the angle defined between the central axis and the imaginary plane may have a magnitude of approximately 90 degrees.

In some embodiments, a pin guide may extend through the superior surface and the inferior surface. Additionally, in some embodiments, the pin guide may extend at a non-orthogonal angle relative to the imaginary plane defined by the inferior surface.

In some embodiments, the cutting guide block may be formed from a semi-transparent polymeric material.

According to another aspect, the orthopaedic surgical instrument system comprises a cutting tool including a shank, a shaft extending distally from the shank, the shaft having a plurality of cutting flutes defined at its distal end, and an outer sleeve pivotally coupled to the shaft such that the shaft and the shank are permitted to rotate relative to the outer sleeve. The system may also comprise a cutting guide block including a slot that defines a cutting guide sized to receive the cutting tool.

In some embodiments, the cutting tool may include at least one roller bearing positioned between the shaft and the outer sleeve to pivotally couple the outer sleeve to the shaft.

In some embodiments, the outer sleeve may include a cylindrical proximal section that has a first diameter, a cylindrical distal section that has a second diameter less than the first diameter, and a middle section connecting the proximal section to the distal section. Additionally, in some embodiments, the cutting tool may include a flange that extends outwardly from the shaft, and the proximal section of the outer sleeve is engaged with the flange.

In some embodiments, the cutting guide block may include a first surface and a second surface positioned opposite the first surface, and the slot may extend through the first surface and the second surface. The slot may be partially defined by a pair of curved surfaces positioned between the first surface and the second surface. The pair of curved surfaces may be shaped to engage the middle section of the outer sleeve of the cutting tool.

In some embodiments, the cutting guide may extend from a first end to a second end, and the slot may have a central axis. When the slot is viewed in cross-section, an angle may be defined between the central axis and an imaginary plane defined by an inferior surface of the cutting guide block. The magnitude of the angle may be non-constant between the first end of the cutting guide and the second end of the cutting guide.

According to another aspect, a method of performing an orthopaedic surgery is disclosed. The method comprises positioning a cutting guide block on an end of a patient's bone, inserting a cutting tool into a slot defined in the cutting guide block such that a cutting angle is defined between the cutting tool and the proximal end of the patient's bone, and advancing the cutting tool along the slot to resect a portion of the proximal end of the patient's bone. The shape of the slot causes the cutting angle to change as the cutting tool advances along the slot.

In some embodiments, inserting the cutting tool into the slot may include advancing an outer shell of the cutting tool into contact with a track surface, and advancing the cutting tool along the slot may include maintaining the outer shell into contact with the track surface and rotating a shaft of the cutting tool relative to the outer shell to resect the portion of the proximal end of the patient's bone.

In some embodiments, the shape of the slot may cause the cutting angle of the cutting tool to decrease as the cutting tool moves from a first end of the slot toward a medial side of the cutting guide block.

In some embodiments, the shaft of the cutting tool may be angled toward a medullary canal of the patient's bone as the cutting tool moves along a section of the slot adjacent to the medial side of the cutting guide block.

In some embodiments, the shape of the slot may cause the cutting angle of the cutting tool to increase as the cutting tool moves from the section of the slot adjacent to the medial side of the cutting guide block toward a lateral side of the cutting guide block.

Additionally, in some embodiments, the method may comprise inserting a bone pin through a pin guide extending through the cutting guide block into the proximal end of the patient's bone at a non-orthogonal angle.

BRIEF DESCRIPTION OF THE DRAWINGS

The detailed description particularly refers to the following figures, in which:

FIG. 6 is a cross-sectional elevation view taken along the line 6-6 in FIG. 3;

FIG. 7 is a cross-sectional elevation view taken along the line 7-7 in FIG. 3;

FIG. 8 is a cross-sectional elevation view taken along the line 8-8 in FIG. 3;

FIG. 9 is a cross-sectional elevation view taken along the line 9-9 in FIG. 3;

DETAILED DESCRIPTION OF THE DRAWINGS

Figure 1:
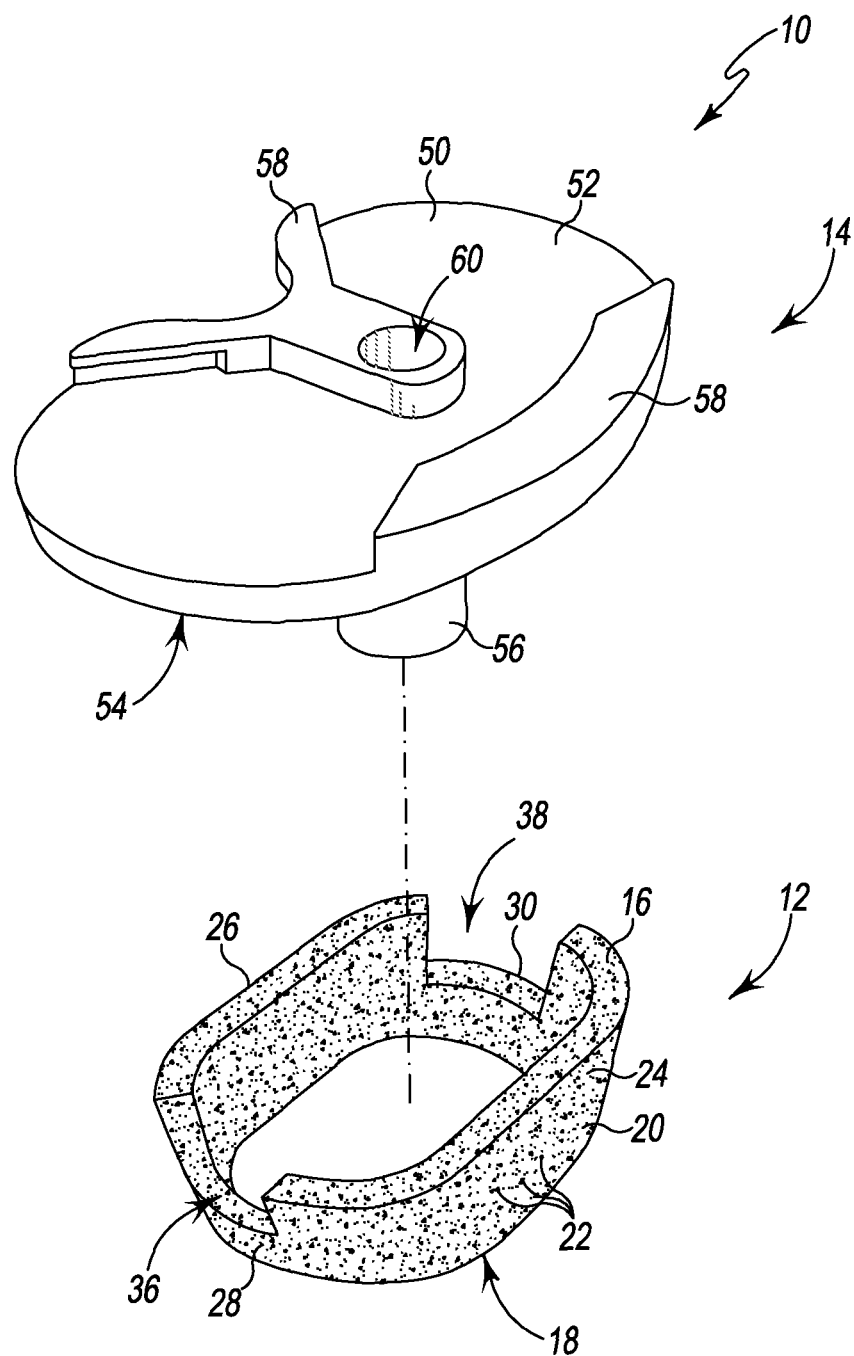
FIG. 1 is an exploded perspective view of an orthopaedic prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. While the disclosure below describes techniques and instrument system in reference to a patient's tibia, it should be appreciated that all of the systems and techniques described below may be used to surgically prepare other bones, such as, for example, a distal end of a patient's femur.

Referring now to FIG. 1, an orthopaedic prosthesis 10 for use in a patient's tibia is shown. In the illustrative embodiment, the orthopaedic prosthesis 10 is configured for use in a primary or a revision total knee arthroplasty and includes a cone implant 12 and a tibial tray 14 configured for implantation into a patient's tibia. Specifically, the cone implant 12 is configured to be secured to a surgically-prepared proximal end of a patient's tibia (see FIG. 16). As described in greater detail below, the surgical instrument system 70 shown in FIG. 2 may be used to define a cavity in the proximal end of a patient's tibia that is sized and shaped to receive the cone implant 12.

As shown in FIG. 1, the cone implant 12 is formed from an implantable metallic material such as, for example, stainless steel, cobalt chromium, titanium, and may be secured to the patient's tibia via use of bone adhesive or other attachment means. The cone implant 12 is annular in shape, and includes a proximal rim surface 16, a distal rim surface 18, and a sidewall 20 extending between the two rim surfaces 16, 18. The sidewall 20 has a number of pores 22 defined therein, which are configured to permit bone ingrowth when the implant 12 is implanted in a patient's bone. In the illustrative embodiment, the sidewall 20 includes an anterior section 24 and a posterior section 26 that are substantially straight. The sections 24, 26 connect a medial section 28 and a lateral section 30 of the sidewall 20. The sections 28, 30 are curved.

The sections 24, 26, 28, 30 of the sidewall 20 are tapered such that the geometry of the implant 12 generally conforms to the geometry of the patient's tibia. As a result, the implant 12 has a proximal maximum medial-lateral width that is greater than its distal maximum medial-lateral width of the cone implant 12. The implant 12 illustratively also includes a pair of notches 36, 38 that are formed in the medial and lateral sections 28, 30, respectively. The notches 36, 38 are sized to accommodate the keels (not shown) protruding from the bottom of the tibial tray 14. It should be appreciated that in other embodiments one or both of the notches 36, 38 may be omitted. In other embodiments, the cone implant 12 may be stepped.

As shown in FIG. 1, the tibial tray 14 is configured to be positioned proximal of the cone implant 12. The tibial tray 14, like the cone implant 12, may be secured to the patient's tibia via use of bone adhesive or other attachment means. The tibial tray 14 is formed from an implantable metallic material such as, for example, stainless steel, cobalt chromium, or titanium.

The tibial tray 14 includes a platform 50 having a top surface 52 and a bottom surface 54. Illustratively, the top surface 52 is generally planar and, in some embodiments, may be highly polished. The tibial tray 14 also includes a stem 56 extending downwardly from the bottom surface of the platform 50. A number of support buttresses 58 extend upwardly from the top surface 52, and each buttress 58 is configured to engage a tibial insert shaped to engage a femoral prosthetic component. A cavity or bore 60 is defined in one of the buttresses 58 and extends downwardly into the stem 56. The bore 60 is formed to receive a complimentary stem of the tibial insert.

Figure 2:
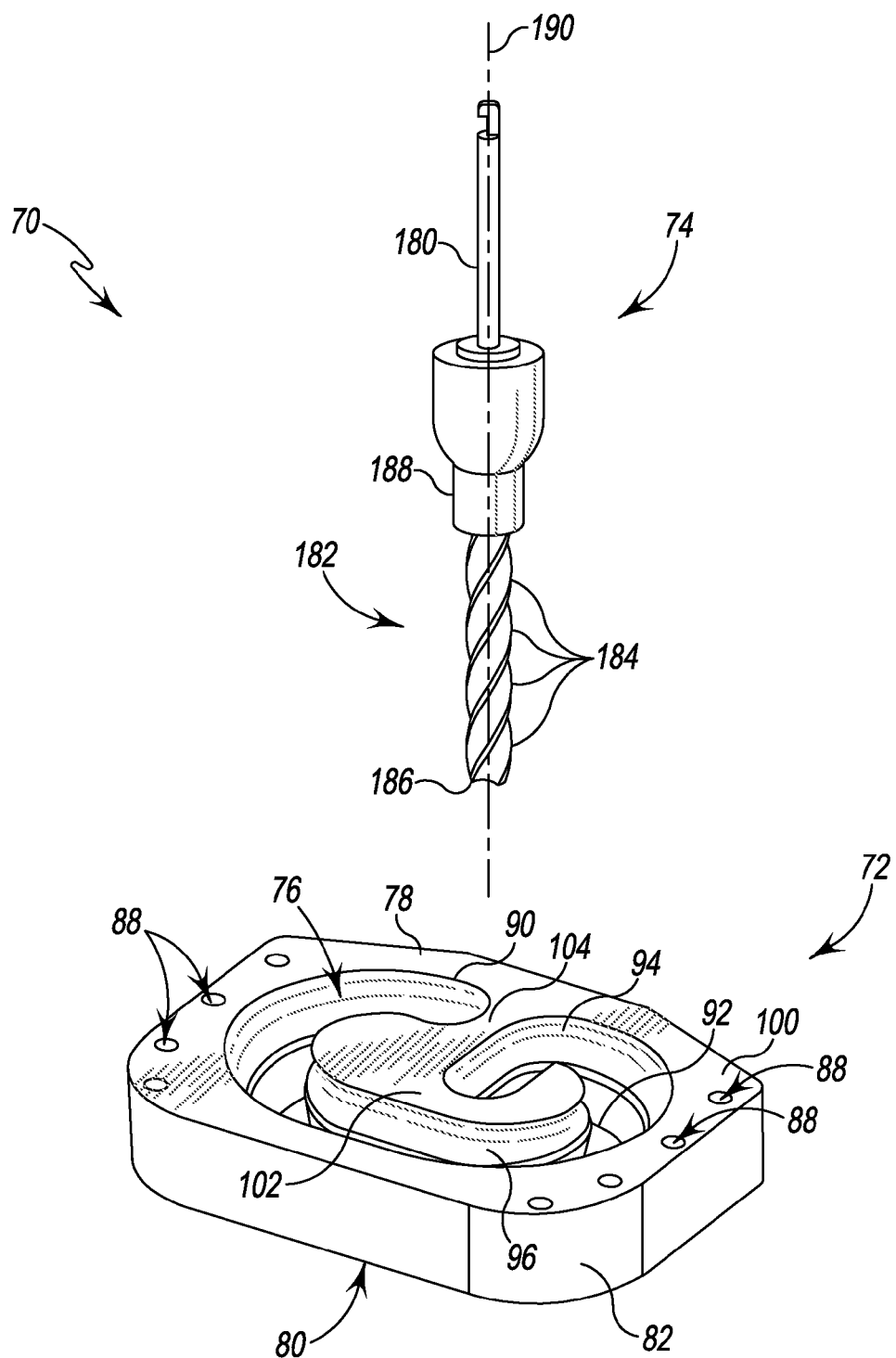
FIG. 2 is an exploded perspective view of an orthopaedic surgical instrument system for use in preparing a patient's bone to receive the orthopaedic prosthesis of FIG. 1.

Referring now to FIG. 2, an orthopaedic surgical instrument system 70 for use in preparing a patient's bone to receive the orthopaedic prosthesis 10 is shown. In the illustrative embodiment, the instrument system 70 includes a cutting guide block 72 and a cutting tool 74 for use with the cutting guide block 72. The cutting guide block 72 includes a cutting guide slot 76 that is sized and shaped to receive the cutting tool 74 and guide the cutting tool 74 to define a cavity that is sized to receive an implant cone 12.

Figure 5:
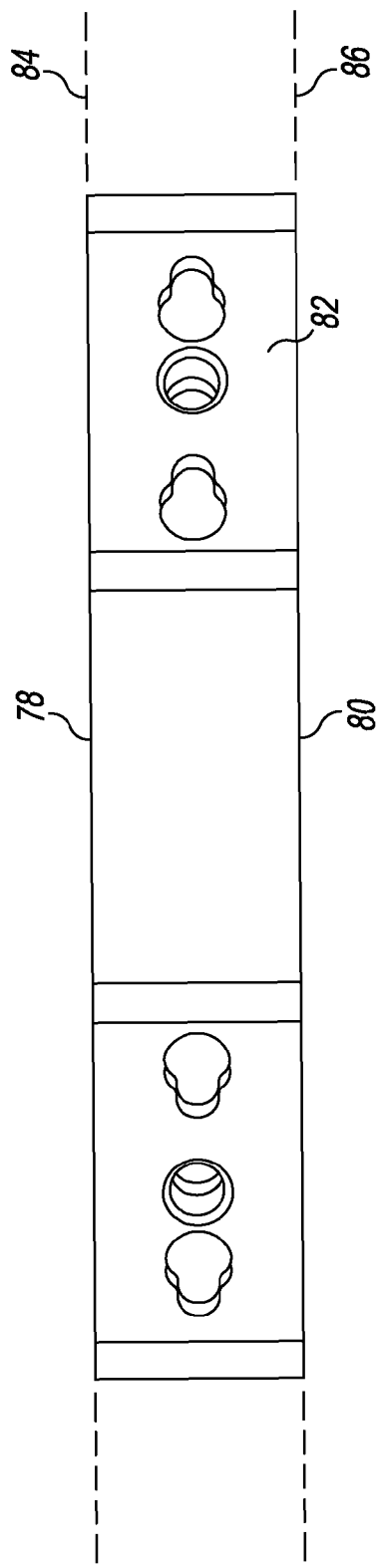
FIG. 5 is a side elevation view of the cutting guide block of FIGS. 4-5.

The cutting guide block 72 includes a superior surface 78, an inferior surface 80 positioned opposite the superior surface 78, and an outer sidewall 82 extending between the two surfaces 78, 80. In the illustrative embodiment, the surfaces 78, 80 are substantially planar surfaces that extend parallel to one another and define imaginary planes 84, 86 (see FIG. 5), which will be discussed in greater detail below in reference to other features of the cutting guide block 72. As shown in FIG. 2, the cutting guide slot 76 extends through the surfaces 78, 80.

In the illustrative embodiment, the cutting guide block 72 is formed from a semi-transparent polymeric material, which permits a surgeon to monitor the cut being made in the patient's bone while also reducing the glare that can be reflected by the cutting guide block 72 when it is placed under bright surgical lights. Examples of suitable semi-transparent polymeric materials are polyetherimide such as, for example, Ultem or polycarbonate such as, for example, Lexan. It should be appreciated that the cutting guide block 72 may be different sizes to fit different sizes of bone, allowing a surgeon to resect a cavity of the correct size in the tibia of the patient.

The cutting guide block 72 also includes a number of fixation pin guides 88 that extend through both the surfaces 78, 80. Each pin guide 88 is sized to receive a bone pin (not shown) to secure the cutting guide block 72 to the patient's bone. In the illustrative embodiment, the pin guides 88 extend through the cutting guide block 72 at a non-orthogonal, or non-perpendicular, angle relative to the surfaces 78, 80.

As described above, the cutting guide slot 76 of the cutting guide block 72 is sized and shaped to receive the cutting tool 74 and guide the cutting tool 74 to define a cavity that is sized to receive an implant cone 12. In the illustrative embodiment, the block 72 includes an opening 90 that is defined in the superior surface 78 and an opening 92 that is defined in the inferior surface 80. A pair of inner walls 94, 96 extends between the openings 90, 92 to define the cutting guide slot 76 in the block 72. The slot 76 extends through the cutting guide block 72 such that the block 72 is divided into an outer body 100, an inner body 102, and a bridging section 104 positioned on the anterior side of the block 72 that connects the bodies 100, 102. In the illustrative embodiment, the outer body 100 includes the inner wall 94, while the inner body 102 includes the opposite inner wall 96.

Figure 3:
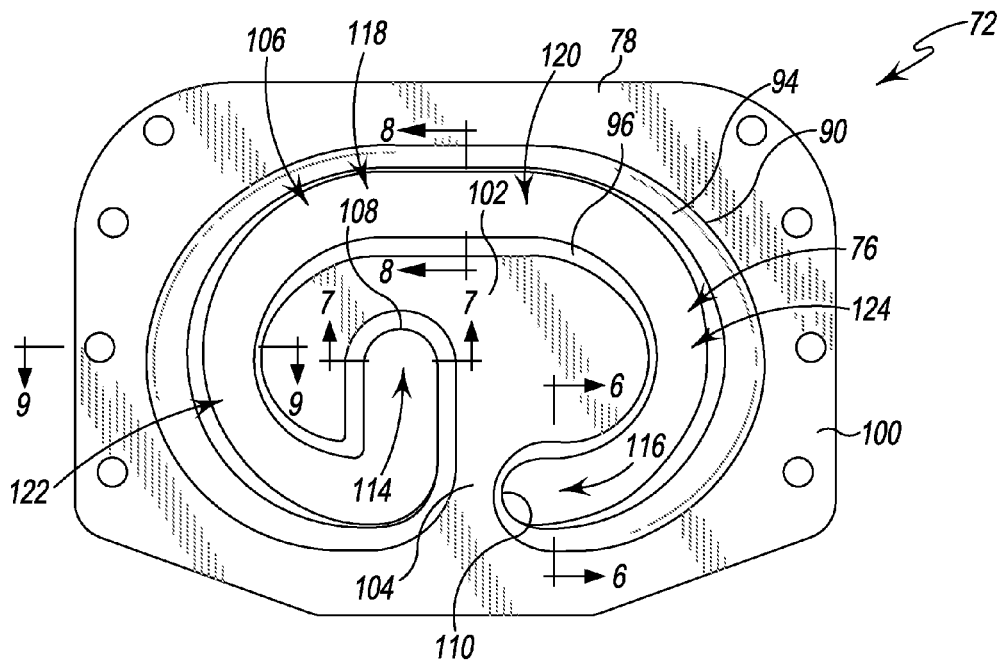
FIG. 3 is a top plan view of a cutting guide block of the surgical instrument system of FIG. 2.
Figure 4:
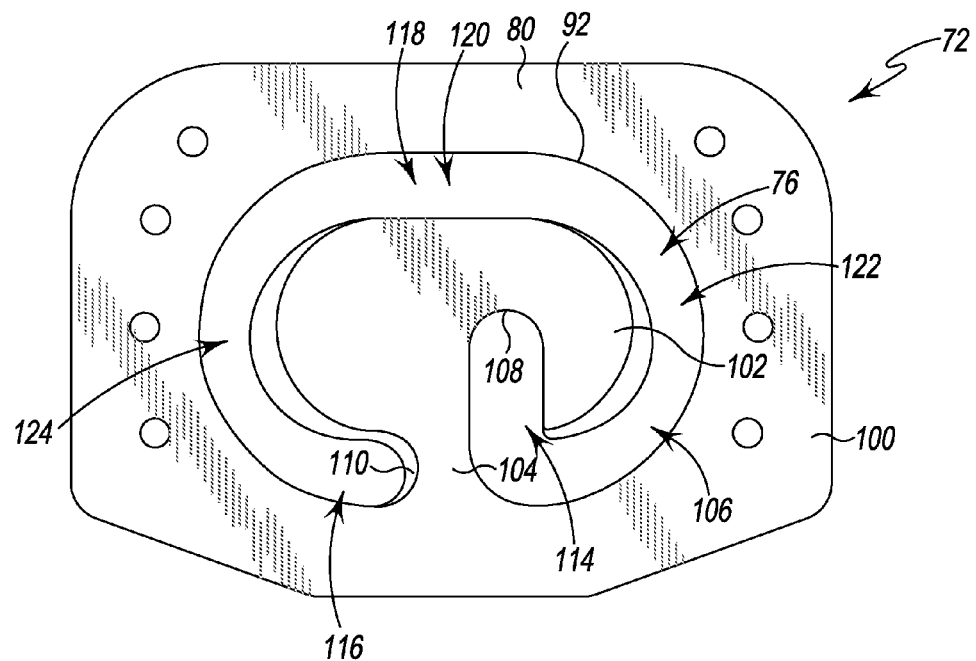
FIG. 4 is a bottom plan view of the cutting guide block of FIG. 3.

As shown in FIGS. 3-4, the cutting guide slot 76 defines a guideway 106 that extends from an end 108 located near the center of the block 72 to another end 110 positioned adjacent the anterior side of the block 72. The guideway 106 defines a cutting path, which the cutting tool 74 follows when resecting a patient's bone. In the illustrative embodiment, the guideway 106 is configured to change the pitch or angle of the cutting tool 74 when it is resecting the patient's bone such that the cutting tool 74 defines a tapered cavity corresponding to the tapered sidewall 20 of the cone implant 12. To do so, the pitch or angle of the guideway 106 relative to the imaginary plane 86 (and hence the inferior surface 80) is adjusted between the ends 108, 110 of the cutting guide slot 76, as shown in FIGS. 6-9 and described in greater detail below.

The guideway 106 is defined by a number of slot sections that vary in pitch relative to the imaginary plane 86. As shown in FIGS. 3-4, for example, the guideway 106 includes a slot section 114 that extends anteriorly from the end 108 of the cutting guide slot 76. In the illustrative embodiment, the section 114 defines a substantially straight cutting path. Another slot section 116 of the guideway 106 extends laterally from the end 110 of the cutting guide slot 76. The slot section 116, like the slot section 114, defines a substantially straight cutting path.

Another slot section 118 connects the sections 114, 116, as shown in FIGS. 3-4. In the illustrative embodiment, the slot section 118 includes a posterior section 120 that extends in a medial-lateral direction and defines a substantially straight cutting path for the cutting tool 74. The slot section 118 also includes a pair of arced sections 122, 124 that connect the posterior section 120 with the slot sections 114, 116, respectively. In the illustrative embodiment, the configuration of the arced section 122 mirrors the configuration of the arced section 124. It should be appreciated that the configuration of the guideway 106 may be adjusted based on the shape of the cone implant 12.

Referring now to FIGS. 6-9, the cutting guide slot 76 is shown in a number of cross-sectional planes 130 extending perpendicular to the surfaces 78, 80 (and hence planes 84, 86) of the cutting block 72 at various points along the slot 76. As described above, the slot 76 is defined by a pair of inner walls 94, 96 extending from a superior opening 90 to an inferior opening 92. In the illustrative embodiment, the inner wall 94 extends from a superior edge 132 that partially defines the superior opening 90 to an inferior edge 134 that partially defines the inferior opening 92. The inner wall 94 includes a curved surface 136 that extends inwardly from the edge 132 to a transition surface 138 positioned between the surfaces 78, 80. Another surface 140 extends from the transition surface 138 to the inferior edge 134. As shown in FIGS. 6-9, the surface 140 defines a substantially straight line 142 when viewed in any of the cross-sectional planes 130.

In the illustrative embodiment, the inner wall 96 extends from a superior edge 150 that partially defines the superior opening 90 to an inferior edge 152 that partially defines the inferior opening 92. The inner wall 96 includes a curved surface 154 that extends inwardly from the edge 150 to a transition surface 156 positioned between the surfaces 78, 80. Another surface 158 extends from the transition surface 156 to the inferior edge 152. As shown in FIGS. 6-9, the surface 158 defines a substantially straight line 160 when viewed in any of the cross-sectional planes 130. In the illustrative embodiment, the line 160 defined by the surface 158 of the inner wall 96 extends parallel to the line 142 defined by the surface 140 of the inner wall 94.

As shown in each of FIGS. 6-9, a width 170 of the opening 90 is defined between the superior edges 132, 150 in each of the cross sectional planes 130. A width 172 of the opening 92 is also defined between the inferior edges 134, 152 in each of the cross sectional planes 130. In the illustrative embodiment, the width 170 is the superior width of the cutting guide slot 76, while the width 172 is the inferior width of the cutting guide slot 76. As shown in FIGS. 6-9, the superior width 170 is greater than the inferior width 172 of the slot 76. As described in greater detail below, the widths 170, 172 are sized to capture the cutting tool 74 and ensure that the cutting tool 74 does not extend into the bone beyond a predetermined depth. It should be appreciated that the widths 170, 172 may not be constant along the length of the guideway 106 and may vary between each of the cross sectional planes 130 shown in FIGS. 6-9.

As shown in FIGS. 6-9, the cutting guide slot 76 has a central axis 174 that is positioned between the inner walls 94, 96. In each of the cross sectional planes 130, the central axis 174 extends parallel to the inferior surfaces 140, 158 of the walls 94, 96, respectively. As described above, the pitch or angle of the guideway 106 relative to the imaginary plane 86 (and hence the inferior surface 80) is adjusted between the ends 108, 110 of the cutting guide slot 76. In the illustrative embodiment, the varying pitch or angle of the guideway 106 is illustrated by the non-constant angles defined between the central axis 174 of the slot 76 and the imaginary plane 86 in the cross sectional planes 130 shown in FIGS. 6-9. For example, as shown in FIG. 6, which is a cross section of the slot 76 taken in an anterior-posterior direction at the end 110 of the slot 76, an angle $\alpha$ is defined between the central axis 174 and the imaginary plane 86. In the illustrative embodiment, the angle $\alpha$ has a magnitude that is slightly less than 90 degrees such that the guideway 106 is pitched inwardly (and hence away from the outer edge of the patient's bone when the block 72 is attached thereto). In that way, the pitch of the guideway 106 at that location corresponds to the taper of the cone implant 12.

As shown in FIG. 7, which is a cross section of the slot 76 taken in a medial-lateral direction at the end 108 of the slot 76, an angle $\beta$ is defined between the central axis 174 and the imaginary plane 86. Because the end 108 is positioned near the center of the block 72 (and hence the center of the patient's bone when the block 72 is attached thereto), it is not necessary for the guideway 106 to be pitched at an angle, and, in the illustrative embodiment, the angle $\beta$ has a magnitude that is approximately 90 degrees.

Similarly, as shown in FIG. 8, which is a cross section of the slot 76 taken in an anterior-posterior direction in the posterior section 120 of the slot 76, an angle $\varphi$ is defined between the central axis 174 and the imaginary plane 86. In the illustrative embodiment, the angle $\varphi$ has a magnitude that is slightly less than 90 degrees such that the guideway 106 is pitched inwardly (and hence away from the outer edge of the patient's bone when the block 72 is attached thereto). In that way, the pitch of the guideway 106 at that location corresponds to the taper of the cone implant 12.

Referring now to FIG. 9, which is a cross section of the slot 76 taken in a medial-lateral direction in one of the arced sections 122 of the slot 76, an angle $\lambda$ is defined between the central axis 174 and the imaginary plane 86. In the illustrative embodiment, the angle $\lambda$ is less than 90 degrees such that the guideway 106 is pitched inwardly (and hence away from the outer edge of the patient's bone when the block 72 is attached thereto). Because of the shape of the patient's tibia and the taper of the cone implant 12, the angle $\lambda$ has a magnitude that is less than the angles $\alpha$, $\varphi$. In the illustrative embodiment, the magnitude of the angle $\lambda$ is in a range of 30 degrees to 70 degrees.

Returning to FIG. 2, the surgical instrument system 70 also includes a cutting tool 74 that may be used with the cutting guide block 72. In the illustrative embodiment, the cutting tool 74 is a burring tool. It should be appreciated that in other embodiments the tool 74 may be reamer, surgical drill, cutting saw blade, or other cutting tool. Additionally, the system 70 may include multiple cutting tools of different lengths to resect different amounts from the patient's bone. Similarly, the system 70 may include cutting guide blocks 72 of different sizes to accommodate different sizes of patient bones.

The cutting tool 74 includes a shank 180 configured to be engaged by a rotary power tool, and a shaft 182 extending distally from the shank 180. The shaft 182 has a plurality of cutting flutes 184 defined at its distal end 186, which are configured to resect the patient's bone. The cutting tool 74 further includes an outer sleeve 188 that is pivotally coupled to the shaft 182 such that the shaft 182 and the shank 180 are permitted to rotate about the tool's longitudinal axis 190 relative to the sleeve 188, as described in greater detail below.

Figure 10:
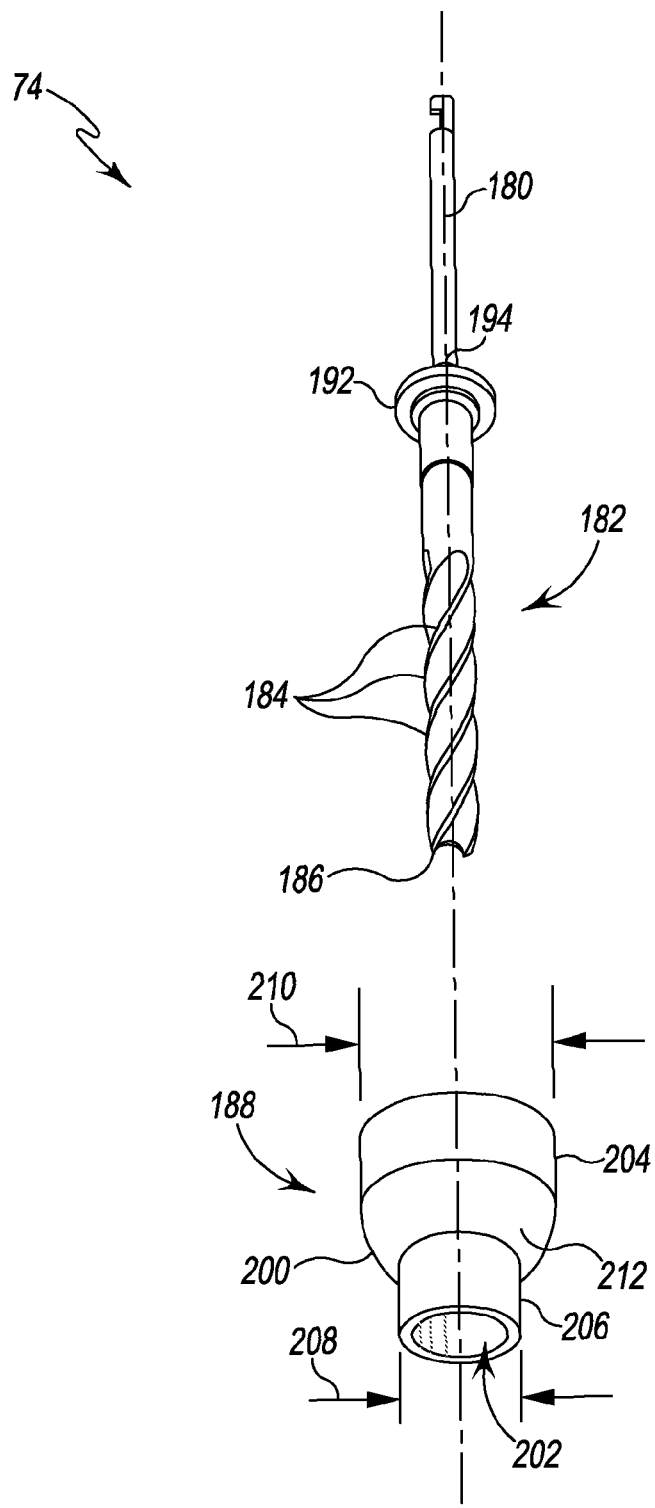
FIG. 10 is an exploded perspective view of a cutting tool of the orthopaedic surgical instrument system of FIG. 2.

Referring now to FIG. 10, the shank 180 of the cutting tool 74 includes a flange 192 that extends outwardly from its distal end 194. The flange 192 provides a stop for the outer sleeve 188 to keep the sleeve 188 engaged with the shaft 182. The sleeve 188 includes a body 200 that has a central passageway 202 defined therein, which is sized to receive the shaft 182. In the illustrative embodiment, the body 200 includes a cylindrical proximal section 204 that engages the flange 192 and a cylindrical distal section 206 that has a diameter 208 that is smaller than the diameter 210 of the proximal section 204. A curved, beveled section 212 connects the sections 204, 206.

Figure 11:
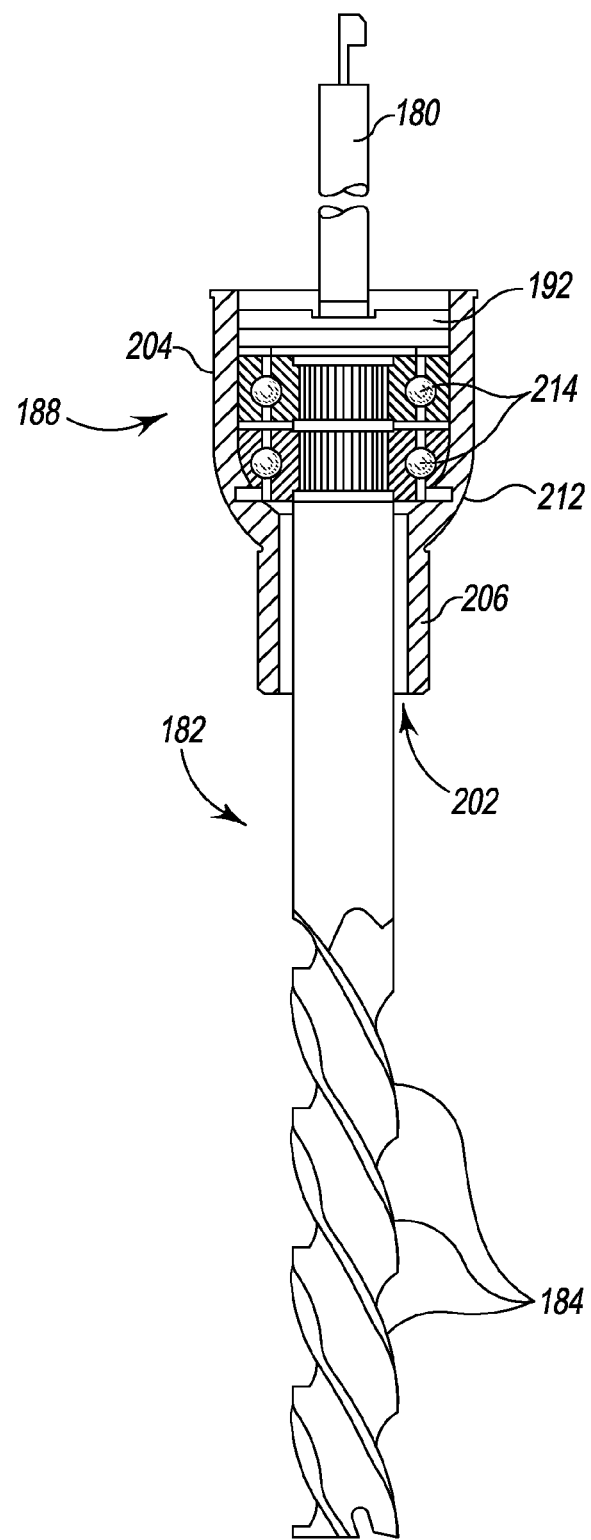
FIG. 11 is a cross-sectional side elevation view of the cutting tool of FIG. 10.

As shown in FIG. 11, the cutting tool 74 also includes a pair of roller bearings 214 that are positioned in the proximal section 204 of the sleeve 188. In the illustrative embodiment, the roller bearings 214 are press-fit into the sleeve 188 and press-fit onto the shaft 182. The roller bearings 214 are configured to permit relative rotation between the outer sleeve 188 and the shaft 182 and the shank 180.

In the illustrative embodiment, the shank 180 and shaft 182 are formed as a single monolithic component from a stainless steel or other metallic material. The sleeve 188 is also formed from a metallic material such as, for example, stainless steel. It should be appreciated that in other embodiments other materials may be used. For example, the sleeve 188 may be formed from a plastic or polymeric material.

Figure 12:
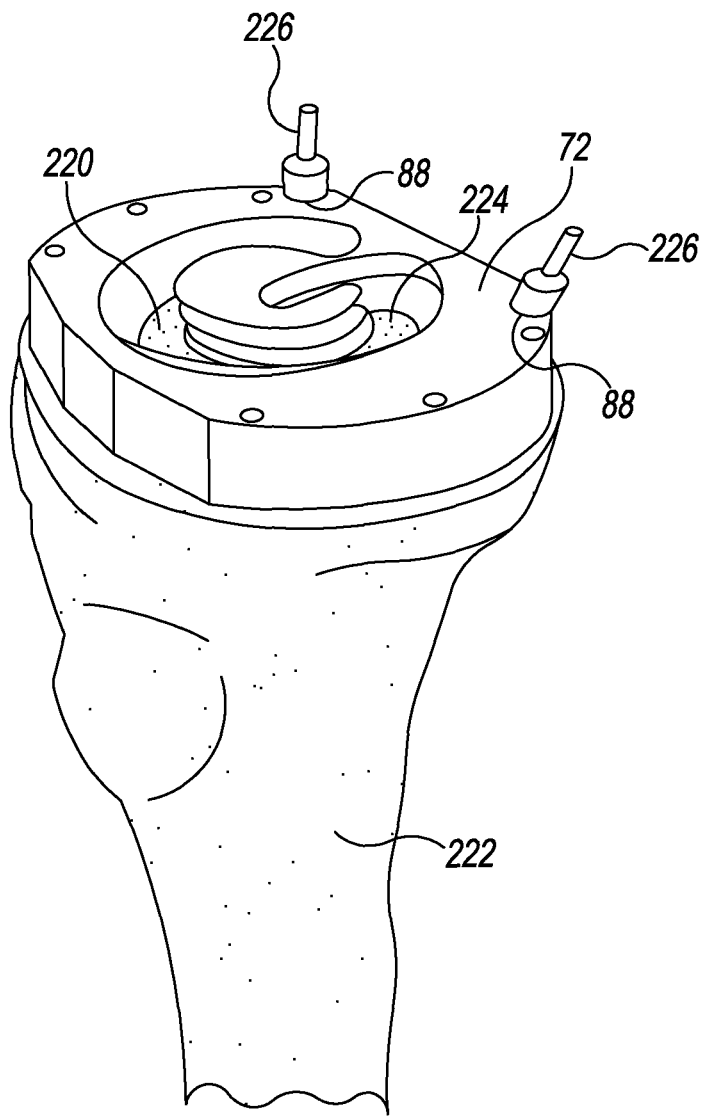
FIGS. 12-16 are illustrations of a surgical procedure for using the orthopaedic surgical instrument system of FIG. 2 in preparing a proximal end of a patient's tibia to receive the orthopaedic prosthesis of FIG. 1.

Referring now to FIGS. 12-16, an exemplary surgical procedure using the system 70 to surgically prepare a proximal end 220 of a patient's tibia 222 to receive a cone implant 12 is shown. In the illustrative embodiment, a reciprocating cutting saw or other cutting tool may be used to create a substantially planar surface 224 on the proximal end 220, as shown in FIG. 12. A surgeon or other user may then place the cutting block 72 on the surface 224. When the block 72 is properly positioned on the tibia 222, the surgeon may advance one or more fixation pins 226 through the fixation pin guides 88 in the block 72. Because the block 72 is formed from a semi-transparent material, the surgeon may monitor the position of the pin tips by looking through the block 72.

With the cutting guide block 72 positioned on the tibia 222, the surgeon may advance the distal end 186 of the cutting tool 74 into the cutting guide slot 76 and into contact with the patient's tibia 222. In the illustrative embodiment, the surgeon may first advance the cutting tool 74 into the end 108 of the cutting guide slot 76. At that position, the distal end 186 of the cutting tool 74 may extend outwardly from the inferior opening 92 of the slot 76 and into the intramedullary canal (not shown) of the tibia 222. The surgeon may continue to advance the cutting tool 74 into the guide slot 76 until the beveled section 212 of the cutting tool's outer sleeve 188 is engaged with the transition surfaces 138, 156 of the cutting block 72, which define a beveled groove 230 sized to receive it (see FIG. 13). When the sleeve 188 is engaged with the transition surfaces 138, 156, the cutting tool's longitudinal axis 190 is coincident with the central axis 174 of the slot 76.

Figure 13:
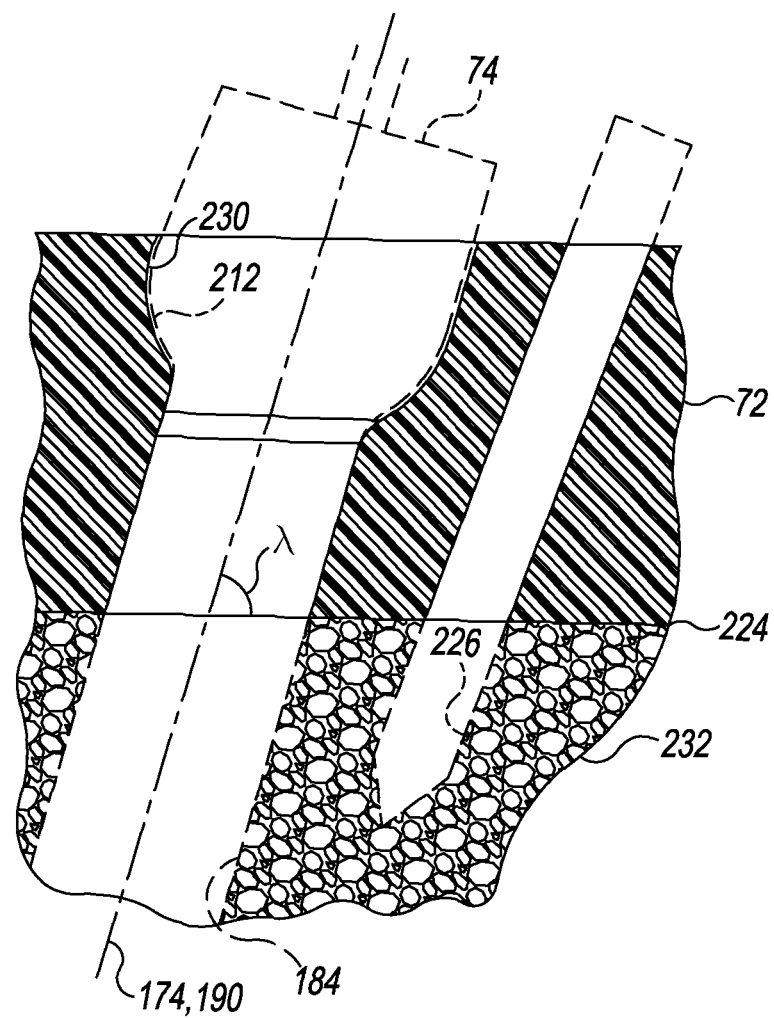

The surgeon may then activate a rotary power tool to cause the shank 180 (and hence the cutting flutes 184) to rotate about the cutting tool's longitudinal axis 190. Because the outer sleeve 188 is pivotally coupled to the shank 180 and the shaft 182, the outer sleeve 188 is isolated from the power tool and does not rotate. While the cutting flutes 184 are rotating and the outer sleeve 188 engaged with the transition surfaces 138, 156, the surgeon may advance the cutting tool 74 anteriorly along the slot section 114 and into contact with the patient's bone. When the surgeon reaches the end of the slot section 114, the surgeon may continue to advance the cutting tool 74 along the arced section 122. As the cutting tool 74 is advanced along the section 122, the pitch of the cutting tool 74 (and hence the cutting angle) changes. As shown in FIG. 13, when a cross section of the slot 76 taken in a medial-lateral direction with the cutting tool 74 is located in the arced section 122, the cutting tool 74 is pitched away from the outer edge 232 of the tibia 222 at the angle $\lambda$, which matches the taper of the cone implant 12 at that position relative to the patient's bone. It should be noted that the same angle $\lambda$ is defined between the cutting tool's longitudinal axis 190 and the resected surface 224.

Figure 14:
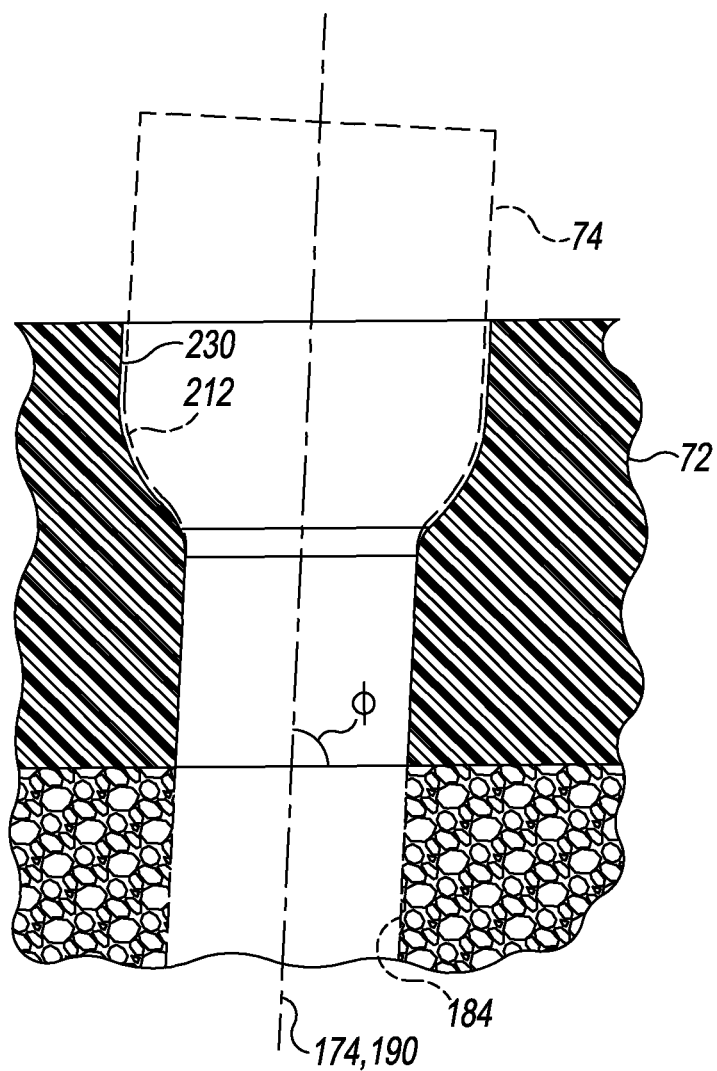

As the cutting tool 74 is advanced along the slot 76, the pitch of the cutting tool 74 is changed. For example, as shown in FIG. 14, which is a cross section of the slot 76 taken in an anterior-posterior direction in the posterior section 120 of the slot 76, the cutting tool 74 is pitched at the angle $\varphi$, which matches the taper of the cone implant 12 at that position relative to the patient's bone. It should be noted that the same angle $\varphi$ is defined between the cutting tool's longitudinal axis 190 and the resected surface 224.

In that way, as the cutting tool 74 is advanced along the slot 76, the pitch of the cutting tool 74 changes to match the corresponding changing taper of the cone implant 12. In the illustrative embodiment, the pitch (and hence the cutting angle) first decreases, then increases, then decreases again, before finally increasing back to slightly less than 90 degrees as the cutting tool 74 is advanced from the end 108 to the end 110 of the cutting guide slot 76.

Figure 15:
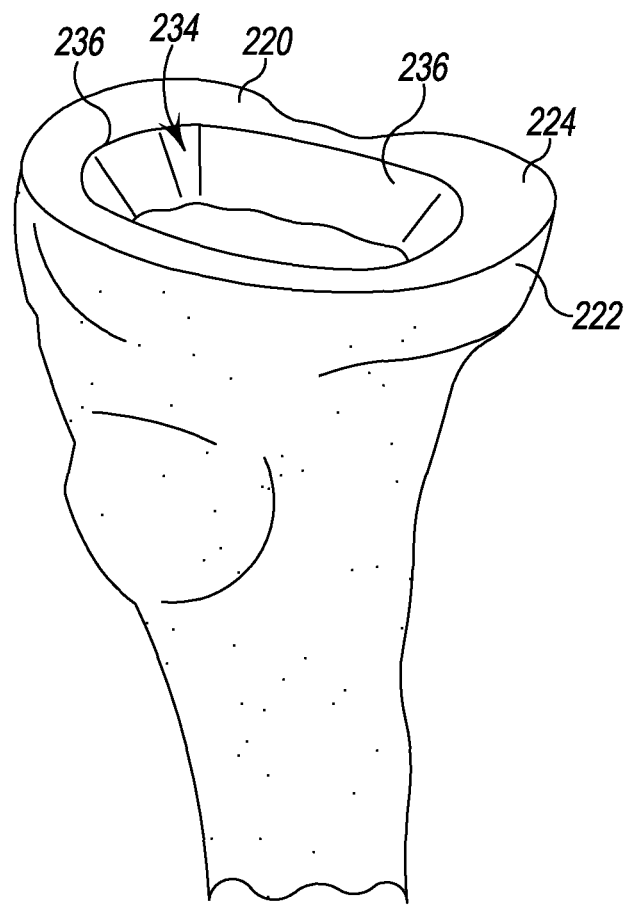
Figure 16:
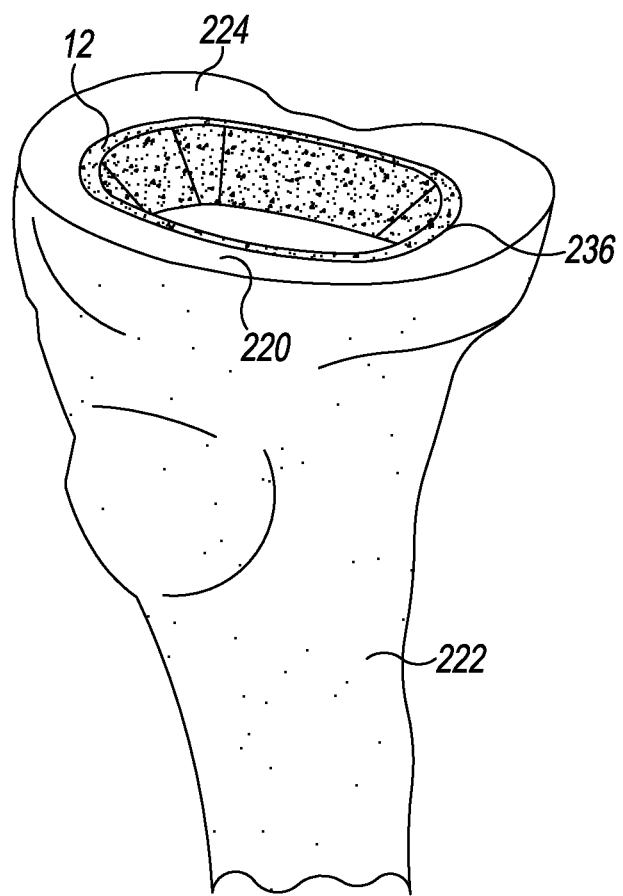

As shown in FIG. 15, when the cutting tool 74 has completed its circuit around the slot 76, a cavity 234 is defined in the surface 220 of the patient's tibia 222, and the cutting tool 74 and the cutting guide block 72 may be removed from the patient's tibia 222. The cavity 234 is defined by a number of walls 236 that are shaped to match the outer geometry of the cone implant 12. As shown in FIG. 16, when the cone implant 12 is positioned in the cavity 234, the cone implant 12 fits snuggly against the walls 236.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument system configured to be used to prepare a proximal end of a patient's tibia to receive an orthopaedic prosthetic component, the orthopaedic surgical instrument system comprising:
   a cutting tool including (i) a shank, (ii) a shaft extending distally from the shank, the shaft having a plurality of cutting flutes defined at its distal end, and (iii) an outer sleeve pivotally coupled to the shaft such that the shaft and the shank are permitted to rotate relative to the outer sleeve, and a cutting guide block sized and configured to be positioned on a surgically-prepared and substantially planar surface of the proximal end of the patient's tibia, the cutting guide block comprising:
  a superior substantially planar surface,
  an inferior substantially planar surface positioned opposite the superior surface, the superior and inferior surfaces extending parallel to one another, the inferior surface being a tibial-contacting surface and defining an imaginary plane, and
  a slot extending through the superior surface and the inferior surface, the slot defining a cutting guide that is sized and shaped to receive the cutting tool, the slot extending from a first end located near the center of the cutting guide block to a second end positioned adjacent an anterior side of the cutting guide block,
wherein the slot divides the cutting guide block into an outer body, an inner body, and a bridging section positioned on the anterior side of the cutting guide block that connects the outer and inner bodies, and when the slot is viewed in a cross-sectional plane extending perpendicular to the imaginary plane at each of a plurality of points between the first end and the second end, (i) the slot has a central axis that extends through the superior surface and the inferior surface, and (ii) an angle is defined between the central axis and the imaginary plane, the magnitude of the angle being non-constant between the first end of the cutting guide and the second end of the cutting guide,
wherein the slot is defined between (i) a first inner wall extending between a first opening defined in the superior surface and a second opening defined in the inferior surface, and (ii) a second inner wall extending between the first opening defined in the superior surface and the second opening defined in the inferior surface,
wherein when the slot is viewed in any cross-sectional plane extending perpendicular to the imaginary plane:
  (i) the central axis is positioned between, and extends parallel to, portions of the first inner wall and the second inner wall,
  (ii) a first width of the slot is defined between a superior edge of the first inner wall and a superior edge of the second inner wall,
  (iii) a second width of the slot is defined between an inferior edge of the first inner wall and an inferior edge of the second inner wall, the second width of the slot being less than the first width,
  (iv) the first inner wall includes a first section extending inwardly from the superior edge of the first inner wall to a transition surface and a second section extending inwardly from the inferior edge of the first inner wall to the transition surface, the first section being curved and the second section defining a straight imaginary line,
  (v) the second inner wall includes a first section extending inwardly from the superior edge of the second inner wall to a transition surface and a second section extending inwardly from the inferior edge of the second inner wall to the transition surface, the first section of the second inner wall being curved and the second section of the second inner wall defining a straight imaginary line extending parallel to the straight imaginary line defined by the second section of the first inner wall, and
  (vi) the transition surfaces define a beveled groove sized to engage the outer sleeve of the cutting tool,
wherein the slot includes:
  a first slot section extending anteriorly from the first end,
  a second slot section extending laterally from the second end, and
  a third slot section connecting the first slot section to the second slot section,
  wherein the third slot section includes (i) a first arced section connected to the first slot section, (ii) a second arced section connected to the second slot section, and (iii) a substantially straight section extending in a medial-lateral direction and connecting the first arced section and the second arced section, and
  wherein the cutting tool is configured to be advanced along the slot to define a cavity in the surgically-prepared and substantially planar surface of the proximal end of the patient's tibia, the cavity being defined by a number of walls that are shaped to match the outer geometry of the orthopaedic prosthetic component.

2. The orthopaedic surgical instrument system of claim 1, wherein:
  when the first arced section of the slot is viewed in a cross-sectional plane extending in a medial-lateral direction perpendicular to the imaginary plane, the angle defined between the central axis and the imaginary plane has a first magnitude, and
  when the straight section of the slot is viewed in a cross-sectional plane extending in an anterior-posterior direction perpendicular to the imaginary plane, the angle defined between the central axis and the imaginary plane has a second magnitude greater than the first magnitude.

3. The orthopaedic surgical instrument system of claim 2, wherein the second magnitude is less than 90 degrees.

4. The orthopaedic surgical instrument system of claim 1, wherein when the first slot section of the slot is viewed in a cross-sectional plane extending in a medial-lateral direction perpendicular to the imaginary plane, the angle defined between the central axis and the imaginary plane has a magnitude of approximately 90 degrees.

5. The orthopaedic surgical instrument system of claim 1, wherein a pin guide extends through the superior surface and the inferior surface.

6. The orthopaedic surgical instrument system of claim 5, wherein the pin guide extends at a non-orthogonal angle relative to the imaginary plane defined by the inferior surface.

7. The orthopaedic surgical instrument system of claim 1, wherein the cutting guide block is formed from a semi-transparent polymeric material.

8. The orthopaedic surgical instrument system of claim 1, wherein the cutting tool includes at least one roller bearing positioned between the shaft and the outer sleeve to pivotally couple the outer sleeve to the shaft.

9. The orthopaedic surgical instrument system of claim 1, wherein the outer sleeve includes (i) a cylindrical proximal section that has a first diameter, (ii) a cylindrical distal section that has a second diameter less than the first diameter, and (iii) a middle section connecting the proximal section to the distal section.

10. The orthopaedic surgical instrument system of claim 9, wherein the cutting tool includes a flange that extends outwardly from the shaft, and the proximal section of the outer sleeve is engaged with the flange.

* * * * *